(12) United States Patent
Chen et al.

(10) Patent No.: US 9,846,257 B2
(45) Date of Patent: Dec. 19, 2017

(54) MOBILE BACK SCATTERING IMAGING SECURITY INSPECTION APPARATUS AND METHOD

(71) Applicants: TSINGHUA UNIVERSITY, Beijing (CN); NUCTECH COMPANY LIMITED, Beijing (CN)

(72) Inventors: Zhiqiang Chen, Beijing (CN); Ziran Zhao, Beijing (CN); Wanlong Wu, Beijing (CN); Yingkang Jin, Beijing (CN); Le Tang, Beijing (CN); Ming Ruan, Beijing (CN); Xiao Tang, Beijing (CN); Guangwei Ding, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 120 days.

(21) Appl. No.: 14/790,947

(22) Filed: Jul. 2, 2015

(65) Prior Publication Data
US 2016/0003966 A1 Jan. 7, 2016

(30) Foreign Application Priority Data
Jul. 4, 2014 (CN) .......................... 2014 1 0320265

(51) Int. Cl.
*G01N 23/201* (2006.01)
*G01V 5/00* (2006.01)
*G01N 23/203* (2006.01)

(52) U.S. Cl.
CPC ......... *G01V 5/0025* (2013.01); *G01N 23/203* (2013.01)

(58) Field of Classification Search
CPC ................. G01N 23/203; G01N 23/04; G01N 23/20083; G01N 23/201; G01N 2223/419;
(Continued)

(56) References Cited

U.S. PATENT DOCUMENTS

| 5,600,700 A | 2/1997 | Krug et al. |
| 6,421,420 B1 * | 7/2002 | Grodzins ............... G01N 23/20 378/113 |

(Continued)

FOREIGN PATENT DOCUMENTS

| CN | 1607386 A | 4/2005 |
| CN | 101883137 A | 11/2010 |

(Continued)

OTHER PUBLICATIONS

European Patent Application No. 15175237.5; Extended Search Report; dated Dec. 4, 2015; 8 pages.

*Primary Examiner* — Irakli Kiknadze
(74) *Attorney, Agent, or Firm* — Baker & Hostetler LLP (57) ABSTRACT

The present disclosure provides a mobile back scattering imaging security inspection apparatus, comprising: a back scattering scanner (2), a detector (3), a controller (4), and a movable stage (1) configured to carry the back scattering scanner, the detector and the controller and being movable with respect to the object to be inspected; wherein the back scattering scanner is a distributed X-ray source comprising a plurality of target points (201), each of which is able to emit the ray beam individually, and wherein the back scattering scanner, the detector and the controller perform an imaging security inspection operation on the object to be inspected during moving along with the movable stage with respect to the object.

19 Claims, 3 Drawing Sheets

(58) Field of Classification Search
CPC ........... G01N 2223/639; G01N 23/005; G01N 23/046; G01N 23/083; G01N 23/087; G01N 23/10; G01V 5/0025; G01V 5/0016; G01V 5/0008; G01V 5/0066; G01V 5/0041; G01V 5/0033; G01V 5/005; G01V 5/0075; G01V 3/10; G01V 3/104; G01V 5/0091; G01V 3/105; G01V 5/00; G01V 5/0058
USPC .................................................. 378/57, 86–90
See application file for complete search history.

(56) References Cited

U.S. PATENT DOCUMENTS

| | | | |
|---|---|---|---|
| 6,459,764 B1 | 10/2002 | Chalmers et al. | |
| 7,505,562 B2* | 3/2009 | Dinca | G01N 23/201 378/57 |
| 2007/0258562 A1 | 11/2007 | Dinca et al. | |
| 2008/0253522 A1* | 10/2008 | Boyden | G01N 23/201 378/87 |
| 2011/0019799 A1 | 1/2011 | Shedlock | |
| 2013/0039472 A1* | 2/2013 | Morton | G01V 5/0041 378/88 |
| 2013/0202089 A1* | 8/2013 | Schubert | G01V 5/0025 378/86 |

FOREIGN PATENT DOCUMENTS

| | | |
|---|---|---|
| CN | 102484935 A | 5/2012 |
| CN | 103892853 A | 7/2014 |
| CN | 204129239 U | 1/2015 |

\* cited by examiner

MOBILE BACK SCATTERING IMAGING SECURITY INSPECTION APPARATUS AND METHOD

CROSS-REFERENCE TO RELATED APPLICATION

This application claims the benefit of Chinese Patent Application No. 201410320265.X filed on Jul. 4, 2014 in the State Intellectual Property Office of China, the whole disclosure of which is incorporated herein by reference.

BACKGROUND OF THE INVENTION

Field of the Invention

The present disclosure generally relates to back scattering imaging technologies, and in particular, relates to a mobile back scattering imaging security inspection apparatus and a method for performing mobile back scattering imaging security inspection.

Description of the Related Art

A conventional mobile X-ray back scattering inspection apparatus for performing an inspection of an interior of an object such as a vehicle typically includes a ray source and a set of detectors. The ray source is typically a single target source with a large spread angle, rays from which are formed into a pencil beam by a rotation modulation mechanism to perform a point by point scanning operation on a surface of the object to be inspected. The detector has a certain spatial dimension to receive scattering signals in a relatively large spatial range.

In the conventional mobile X-ray back scattering inspection apparatus, a flying spot scanning mechanism configured to modulate the rays to form scanning flying spots is typically a wheel-type flying spot scanning mechanism. By providing a roller wheel provided with a modulation aperture around the source, the pencil ray beam is formed. The pencil ray beam is used for one dimensional scanning operation on the surface of the object to be scanned as the roller wheel rotates. In the apparatus using the wheel-type flying spot scanning mechanism, dimensions and spatial distribution of the ray spots formed by the flying spot mechanism on the surface to be inspected change, in particular have a distortion at the large spread angle, as a modulation spread angle varies. Thus, the spread angle of the ray source is limited. Also, in order to ensure an imaging range, there is a certain requirement for a distance between the ray source and the surface of the object to be scanned.

Furthermore, for an integral mobile system formed by coupling the ray source and the detector, the distance between the ray source and the object to be scanned must influence the distance between the detector and the object to be scanned. An increase in the distance between the detector and the surface of the object to be scanned will influence the spatial coverage of the detector.

In view of the above, it is desired to propose a novel mobile X-ray back scattering imaging apparatus and method.

SUMMARY OF THE INVENTION

The present disclosure is intended to overcome at least one aspect of the above problems and defects in the prior art.

An embodiment of the present invention provides a mobile back scattering imaging security inspection apparatus, comprising:

a back scattering scanner configured to emit a ray beam for scanning an object to be inspected:

a detector configured to receive a back scattering ray of the ray beam for scanning the object to be inspected;

a controller configured to control the back scattering scanner so that the back scattering scanner emits the ray beam for scanning the object to be inspected; and a movable stage configured to carry the back scattering scanner, the detector and the controller and being movable with respect to the object to be inspected:

wherein the back scattering scanner comprises a distributed X-ray source and a collimator, the distributed X-ray source comprising a plurality of target points, each of which is able to emit the ray beam individually, the ray beam emitted from each of the target points being collimated by the collimator into at least one pencil ray beam; and wherein the back scattering scanner, the detector and the controller perform an imaging security inspection operation on the object to be inspected during moving along with the movable stage with respect to the object.

In an embodiment, the plurality of target points may be arranged in one row in a direction perpendicular to a movement direction of the movable stage.

In an embodiment, the controller may be configured to control the back scattering scanner such that the plurality of target points emit the pencil ray beams in a predetermined order.

In an embodiment, the controller may be configured to control the back scattering scanner such that only one of the plurality of target points emits the pencil ray beam at a time during scanning the object to be inspected.

In an embodiment, the controller may be configured to control the back scattering scanner such that at least two of the plurality of target points emit the pencil ray beams at a time during scanning the object to be inspected.

In an embodiment, the mobile back scattering imaging security inspection apparatus may further comprise one or more distance measuring devices configured to measure in real-time a distance between a surface of the detector for receiving the back scattering ray and a ray incidence face of the object to be inspected.

In an embodiment, the controller may be configured to determine the target points, from which the pencil ray beams are simultaneously emitted, among the plurality of target points, on the basis of the distance measured by the distance measuring devices.

In an embodiment, the distance measuring devices may be configured to measure a height of the object to be inspected such that the controller controls the target point at a corresponding height to emit the ray beam according to the detected height of the object.

In an embodiment, the detector may comprise a plurality of strip detecting units arranged in a direction perpendicular to a movement direction of the movable stage.

In an embodiment, a collimator may be arranged inserted into a certain depth between every two detecting units, the collimator being configured to reduce mutual interference of the back scattering rays at different flying spots on the object to be inspected.

An embodiment of the present invention provides a method for performing a mobile back scattering imaging security inspection operation by using a mobile back scattering imaging security inspection apparatus, the apparatus comprising a back scattering scanner, a detector, a controller, and a movable stage configured to carry the back scattering scanner, the detector and the controller, the back scattering scanner comprising a distributed X-ray source and a collimator, the distributed X-ray source comprising a plurality of target points, a ray emitted from each of the target points being collimated by the collimator into at least one pencil ray beam, the method comprising:

(a) positioning a ray emergence face of the movable stage to face towards a surface to be inspected of an object to be inspected with a certain distance therebetween;

(b) moving the movable stage in a predetermined direction with respect to the object while keeping the ray emergence face of the movable stage parallel to the surface to be inspected;

(c) controlling the back scattering scanner by the controller so that the plurality of target points emits the pencil ray beams in a predetermined order so as to achieve scanning of a row of flying spots corresponding to the plurality of target points on the object to be inspected and to acquire pixel data of the row of flying spots; and (d) scanning a region to be inspected of the object to be inspected row by row by using the back scattering scanner as the movable stage moves with respect to the object, and splicing the pixel data of each row of flying points by the controller into an entire image of the region being inspected.

In an embodiment, the mobile back scattering imaging security inspection apparatus may further comprise one or more distance measuring devices configured to measure in real-time the distance between a surface of the detector for receiving the back scattering ray and a ray incidence face of the object to be inspected, and in the step (c), the controller controls the back scattering scanner on the basis of the distance measured by the distance measuring devices such that more than one target point emits the pencil ray beam at a time.

In an embodiment, the distance measuring devices may be configured to measure a height of the object to be inspected, and the controller may be configured to control the target point with a corresponding height to emit the ray beam according to the detected height of the object.

In an embodiment, in the step (b), the movable stage is kept stationary while the object to be inspected moves in a predetermined direction with respect to the movable stage.

In the present disclosure, the distributed X-ray source is used, thus when the object is scanned row by row, each ray spot is emitted from the target point closest to the position to be scanned of the object, and the spread angle of the ray beam, which is formed by the ray beam's trace, is approximately parallel to the horizontal direction Thus, there is a less variation, in longitudinal direction, of size and intensity of the ray spot formed on the surface of the object to be inspected, and the formed spot becomes more uniform so as to improve the imaging quality of the edge part of the object to be inspected.

Further, in a simultaneous multiple point scanning way, the speed of scanning the object to be inspected may be increased efficiently so as to reduce the time required for security inspection significantly.

BRIEF DESCRIPTION OF THE DRAWINGS

The following drawings show embodiments of the present invention. The embodiments provided by the following description and drawings are only given by ways of examples, instead of being intended to limit the present invention.

DETAILED DESCRIPTION OF PREFERRED EMBODIMENTS OF THE INVENTION

Exemplary embodiments of the present disclosure will be described below in detail. It should be noted that the embodiments herein are given by ways of examples, instead of limiting the present invention. In the following description, a great deal of specific details is explained in order that the present disclosure may be understood thoroughly. However, the skilled person in the art would apparently appreciate that the present invention is not limited by these specific details. In other examples, in order to avoid confuse the present disclosure, the well-known structures, materials or methods are not described specifically.

Throughout the description, references to "an embodiment", "embodiments", "an example" or "examples" mean that specific features, structures or characteristics described with reference to the embodiment or example are contained in at least one embodiment of the present invention. Thus, throughout the description, phrases such as "in an embodiment", "in embodiments", "in an example" or "in examples" do not necessarily refer to the same one embodiment or example. In addition, the specific features, structures or characteristics may be combined in one or more embodiments or examples in any suitable combination and/or sub-combinations. Further, it should be noted that the term "and/or" used herein includes any one of one or more items listed and all combinations thereof.

First Embodiment

Figure 1:
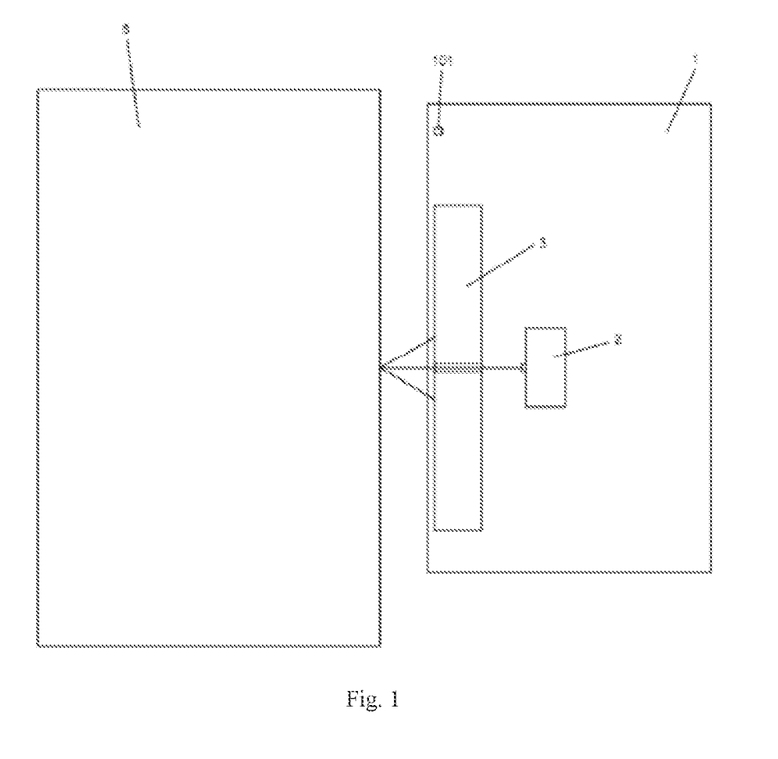
FIG. 1 is a top view schematically showing a mobile back scattering security inspection apparatus according to an embodiment of the present invention.
Figure 2:
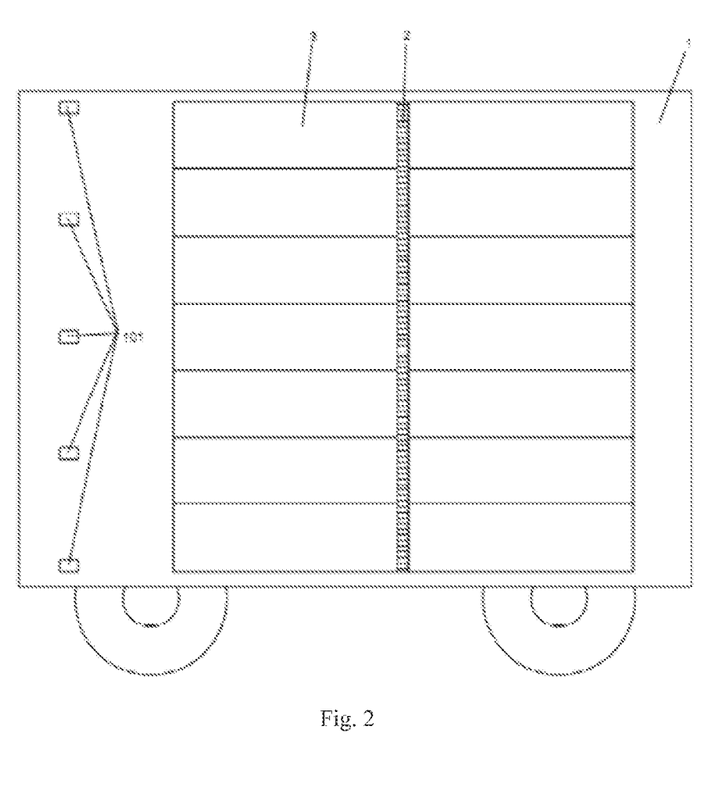
FIG. 2 is a side view schematically showing a mobile back scattering security inspection apparatus according to an embodiment of the present invention.
Figure 3:
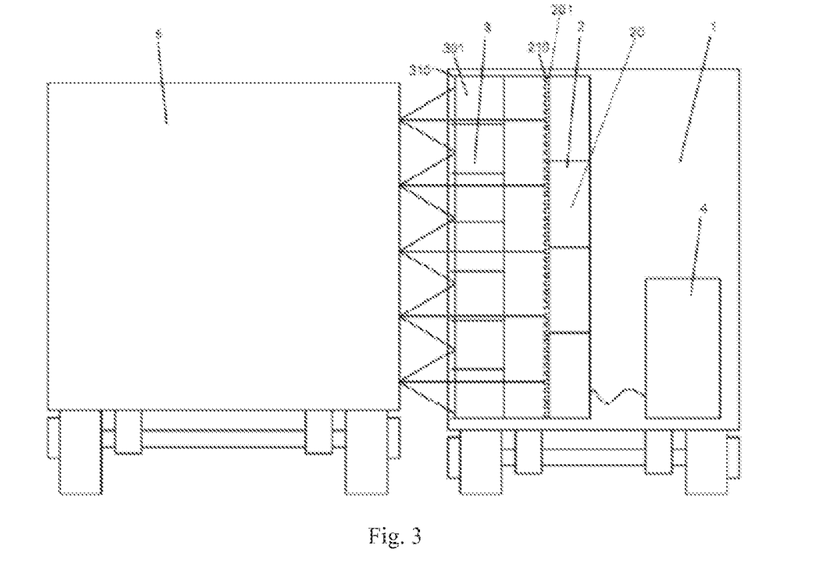
FIG. 3 is a rear view schematically showing a mobile back scattering security inspection apparatus according to an embodiment of the present invention.

As illustrated in FIGS. 1-3, a mobile back scattering imaging security inspection apparatus is provided according to an embodiment of the present invention. It includes a back scattering scanner 2, a detector 3, a controller 4 and a movable stage 1.

With reference to FIGS. 1-3, the back scattering scanner 2, the detector 3 and the controller 4 are arranged on the movable stage 1 and are movable along with the movable stage 1 with respect to an object 5 to be inspected. In the embodiment, the object 5 to be inspected is a vehicle. Certainly, the object 5 to be inspected is not limited to the vehicle, but may be any movable or fixed object in which loads are carried.

In the embodiment, the back scattering scanner 2 is a distributed X-ray source 20 which includes a plurality of target points 201. The plurality of target points 201 are arranged in one row in a direction (vertical direction) perpendicular to a movement direction (horizontal direction) of the movable stage 1. The number of the target points is not limited, and may be provided depending on the height of the object to be inspected. In the distributed X-ray source 20 including the plurality of target points 201, the respective target points 201 have an ability of emitting ray individually and may emit rays respectively in a particular order, or rays are emitted simultaneously from several points, under control of an external control signal. In addition, the back scattering scanner 2 further includes a collimator 210 arranged in front of the distributed X-ray source. The collimator 210 may collimate the ray emitted from each target point into at least one pencil ray beam.

In the embodiment, each target point in the X-ray source is provided with a collimating member configured to modulate the X-ray. The collimating member is located in front of the target point and allows the beam emitted from each target point to form two beams of pencil X-ray simultaneously that are projected onto two position on the vehicle 5 to be inspected after it passes through the collimating member. In the embodiment, since the collimating member for emitting two beams of pencil X-rays simultaneously is provided for each target point, each scan operation in fact achieves two projections of the X-ray to the object to be inspected, and thus two scattering signals could be acquired. By means of processing the acquired signals, an image of the object to be inspected, which has an improved entirety and higher contrast, may be achieved in one scan operation; or a higher scanning speed may be achieved.

Certainly, as desired, each target point may emit other number of ray beams simultaneously through the collimator.

In the embodiment, the controller 4 is configured to control the back scattering scanner 2 such that the plurality of target points 201 emit the pencil ray beams in a predetermined order. For example, the plurality of target points 201 emit the pencil ray beams in order from up to down to achieve a series of scans on the region to be inspected of the vehicle 5. In some applications, the height of the object to be inspected may be greater than the distribution length of a single ray source. In this case, a plurality of distributed ray sources may be spliced together in the lengthwise direction thereof to form the distributed ray source with a desired length.

In the shown embodiment, the detector 3 consists of a plurality of detector units 301 laminated vertically. The detector unit 301 preferably has a strip shape having a long side arranged along a horizontal direction. Each two adjacent ones of the detector units 301 are joined by adjoining their adjacent long sides to form the detector 3. The number of the detector units 301 may be close to or less than the number of the ray source target points. As an example, two adjacent ones of the detector units 301 may be separated from each other by a collimating sheet 310 inserted between them by a certain depth, which contributes to reduction in mutual interference among scattered rays from different flying spots.

In the embodiment, when the mobile back scattering image security inspection apparatus is used to scan the vehicle 5 to be inspected, the controller 4 controls the plurality of target points to emit the pencil ray beams in order from up to down to achieve a series of scans on the region to be inspected of the vehicle 5 during scanning, only one of the target points emits the ray each time, thus, the controller 4 may acquire the pixel data of the flying spot corresponding to the target point by summarizing reading from all of detector units 301 at the moment at which each target point emits the ray. After the series of scans, the pixel data of the row of flying spots can be acquired. Then, the region to be inspected of the vehicle 5 is scanned row by row as the movable stage 1 moves, and finally, after the movable stage 1 passes by the vehicle 5 to be inspected, the pixel data of each row of flying spots are spliced together to obtain an entire image of the region being inspected.

A method for performing mobile back scattering imaging security inspection is also according to an embodiment. The method includes the following steps:

(a) positioning the movable stage 1 so that its ray emergence face faces towards a surface to be inspected of an object to be inspected with a certain distance therebetween;

(b) moving the movable stage 1 in a predetermined direction with respect to the object while keeping the ray emergence face of the movable stage 1 parallel to the surface to be inspected;

(c) controlling the back scattering scanner 2 by the controller 4 so that the plurality of target points 201 emit the pencil ray beams in a predetermined order so as to achieve scanning of a row of flying spots corresponding to the plurality of target points 201 on the object to be inspected and to acquire pixel data of the row of flying spots; and (d) scanning a region to be inspected of the object to be inspected row by row by using the back scattering scanner 2 as the movable stage 1 moves with respect to the object, and splicing the pixel data of each row of flying points by the controller 4 into an entire image of the region being inspected.

In the embodiment, the target points in the distributed ray source are distributed in one row in space, thus when the object is scanned row by row, each spot is emitted from the target point closest to the scanned position and the ray beam has a spread angle formed by its trace which is approximately parallel to the horizontal direction. In contrast, in the case of a single target point source, a larger emitting angle is needed at two ends of an image. Thus, in comparison with the case of single target point source, the distributed ray source including the plurality of target points in accordance with the embodiment has a less variation, in longitudinal direction, of size and intensity of the ray spot formed on the surface of the object to be inspected, and the formed light spots are distributed more uniformly so as to improve the imaging quality of the edge part of the object to be inspected.

In the embodiment, when the object to be inspected is scanned row by row, only one target point emits the pencil ray beam each time (also called as single point scan), and the distance between the detector and the object may not be considered. The scattered rays for each scan point (flying spot) are received by an entire area of the detector. Such scanning way has a defect, that is, it needs too long time to complete the scanning operation.

Second Embodiment

When the object to be inspected is scanned by the X-ray, the ray will be attenuated rapidly inside the object to be inspected as the incidence depth increases. Thus, the back scattering image mainly exhibits the information about structures in superficial layer on the surface of the object to be inspected. The larger the depth becomes, the less the information it can exhibit. In addition, for each flying spot (i.e., scan point), all of the rays scattered by the object are mainly distributed in a certain spread angle range and the part of the rays impacting on the surface of the detector is mainly distributed within a certain area at a position just facing the flying spot while few rays are distributed away from the flying spot.

In view of the two aspects, it may be considered to cause a plurality of target points in the distributed ray source to emit rays simultaneously at a time and the scattered rays at the flying spots corresponding to two adjacent target points for simultaneously emitting rays do not have mutual interference on the surface of the detector or keep the mutual interference in a receivable range.

The main distribution range of the scattered rays for single flying spot on the surface of the detector depends on the distance between the object to be inspected and the surface of the detector. The relation between the main distribution range and the distance may be determined by Monte Carlo Simulation or measurements in experiments. If the relation has been determined, the distance between two closest points for simultaneously emitting rays can be determined through the relation.

Figure 4:
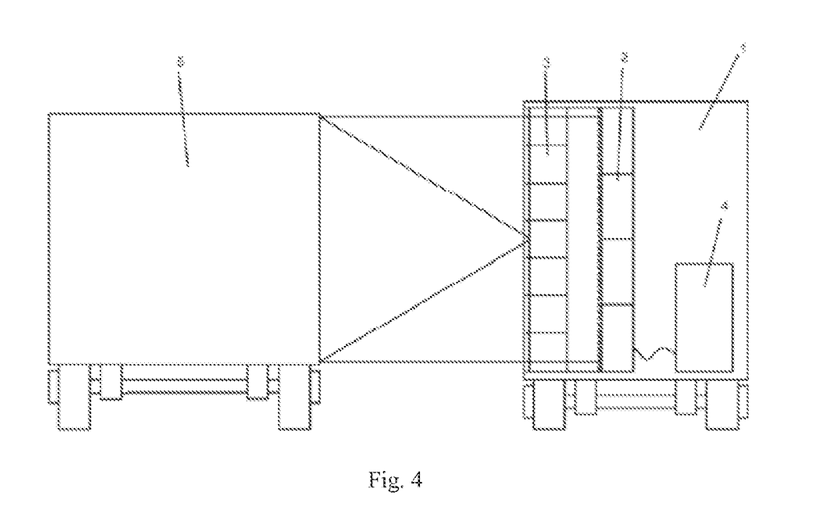
FIG. 4 is a schematic view showing a mobile back scattering security inspection apparatus according to an embodiment of the present invention in a state that it is farther away from an object to be inspected.

Thus, the second embodiment provides a mobile back scattering security inspection apparatus that may use a plurality of target points to emit rays simultaneously. The mobile back scattering security inspection apparatus provided according to the second embodiment is different from the first embodiment in that it further includes one or more distance measuring devices 101 configured to measure in real-time a distance between a surface of the detector for receiving back scattering ray and a ray incidence face of the object to be inspected. Other components are the same as those of the mobile back scattering security inspection apparatus according to the first embodiment.

The controller 4 is configured to determine the distance between two closest target points for simultaneously emitting rays on the basis of the distance measured by the one or more distance measuring devices 101, and then determine the target points for simultaneously emitting rays on the basis of the distribution length of the entire ray source.

In an example, assuming that the number of the target points in an entire radioactive source system is $N_t$, the distance between two adjacent target points is S and the distance between two closest points for simultaneously emitting rays is D, the number N of the target points for simultaneously emitting rays is $$N=N_t*S/D$$

When the distance between the movable stage 1 and the object to be inspected is small, the number of the target points for simultaneously rays is large. When the distance between the movable stage 1 and the object to be inspected is large, the number of the target points for simultaneously rays is small, and in particular, when the distance exceeds a certain threshold, only one target point emits rays at a time. It is the conventional single target point X-ray source.

The detector 3 records signal readings from respective detector units at each moment, and then the controller 4 calculates the covering range of the scattered ray for each target point at each moment. The pixel data of the flying spot corresponding to the target point can be acquired by summarizing the readings in the covering range.

For example, if the distance between the target points for simultaneously emitting is D and the number of the target points is N, the control system 4 controls the target points in each area to emit rays in sequence. The target points are controlled to emit rays in an initial order of 1st, ((D/S)+1)th, (2(D/S)+1)th, . . . , ((N−1)(D/S)+1)th, then at the next time in a order of 2nd, ((D/S)+2, 2(D/S)+2)th, . . . , ((N−1)(D/S)+2) th, and finally, in a order of (D/S)th, 2(D/S)th, 3(D/S)th, . . . , N (D/S)th, so as to complete a row of scans. For the case that the number of the target points is not an integer multiple of the distance, the number of the target points for emitting rays in the last area may be reduced correspondingly.

The detector 3 records signal reading from respective detector units at each moment. The controller 4 records conditions of emitting of the target points in the distributed ray source at each corresponding moment, and summarizes the readings of back scattering signals of the detector 3 that are read in the covering range of the scattered rays from the same target point so as to obtain the pixel data of the flying spot corresponding to the target point. As an example, when the first target point emits the ray, the readings from the detector units 301 in the positions corresponding to the first target point to the (1+D/S2)th target point are summarized to obtain the pixel data of the flying spot corresponding to the first target point. Data in each area are spliced together to obtain a row of complete data.

In addition, two sets of imaging systems may be arranged on either side of the movable stage 1 to achieve the scans on either side.

Further, in accordance with a preferable embodiment, the distance measuring devices 101 are configured to measure a height of the object to be inspected such that the controller 4 controls the target point 201 at the corresponding height to emit the ray beam according to the detected height of the object. In this way, the target points 201 at different heights may be controlled to emit rays according to the difference in heights of the object to be inspected.

For example, if the object to be inspected has a relatively small height, only the target points within the height range of the object to be inspected are controlled to emit rays while the target points that do not fall within the height range of the object to be inspected do not emit rays. Thus, the detecting efficiency is improved.

An embodiment of the present disclosure also provides a method for performing mobile back scattering imaging security inspection. The method includes the following steps:

(a) positioning a ray emergence face of the movable stage 1 to face towards a surface to be inspected of an object to be inspected with a certain distance therebetween;

(b) moving the movable stage 1 in a predetermined direction with respect to the object while keeping the ray emergence face of the movable stage 1 parallel to the surface to be inspected;

(c) controlling the back scattering scanner 2 by the controller 4 on the basis of the distance measured by the distance measuring devices 101 so that the plurality of target points 201 emit pencil ray beams in a predetermined order, and controlling more than one target point to emit the pencil ray beams at a time so as to achieve scanning of a row of flying spots corresponding to the plurality of target points 201 on the object to be inspected and to acquire pixel data of the row of flying spots; and (d) scanning a region to be inspected of the object row by row by using the back scattering scanner 2 as the movable stage 1 moves with respect to the object, and splicing the pixel data of each row of flying points by the controller 4 into an entire image of the region being inspected.

In this embodiment, the plurality of target points of the back scattering scanner 2 are controlled by the controller 4 such that the plurality of target points emit the pencil ray beams simultaneously at a time, that is, simultaneous multiple point scans are achieved. In comparison with the mode of single point scan, it may improve the scanning speed efficiently. In the single point scan mode, the distance between the detector and the object to be inspected is not considered, and for scattered rays from each flying spot, the back scattering signals are received by an entire area of the detector. When the object to be inspected is close to the detector, only part of area is the efficient receiving area. In this embodiment, the number of flying spots for scanning simultaneously is determined according to the measured distance, and the plurality of flying spots may scan the object simultaneously when the object to be inspected is close to the detector so as to achieve the scanning operation at a speed several times higher than the speed in the single point scan.

In the above embodiments, the object to be inspected remains stationary while the imaging security inspection operations are achieved by moving the movable back scattering imaging security inspection apparatus. The present invention is not limited to this. For example, in some alternative embodiments, when the security inspection operation is performed on some movable vehicles, the mobile back scattering imaging security inspection apparatus remains stationary while the vehicle to be inspected moves with respect to the mobile back scattering imaging security inspection apparatus. The back scattering scanner 2 may achieve the imaging the security inspection operations on the vehicle in the same scanning manner row by row.

Although several exemplary embodiments have been shown and described, the present invention is not limited to those and it would be appreciated by those skilled in the art that various changes or modifications may be made in these embodiments without departing from the principles and spirit of the disclosure, the scope of which is defined in the claims and their equivalents.

What is claimed is:

1. A mobile back scattering imaging security inspection apparatus, comprising:
    a back scattering scanner (2) configured to emit a ray beam for scanning an object to be inspected, the back scattering scanner (2) comprising a distributed X-ray source and a collimator (210), the distributed X-ray source comprising a plurality of outgoing target points (201), each of which is able to emit the ray beam individually, the ray beam emitted from each of the target points being collimated by the collimator into at least one pencil ray beam;
    a detector (3) configured to receive a back scattering ray of the ray beam for scanning the object to be inspected;
    a distance measuring device configured to measure in real-time a distance between a surface of the detector for receiving the back scattering ray and a ray incidence face of the object to be inspected;
    a controller (4) configured to, based on the distance measured by the distance measuring device, select and control one or more of the plurality of outgoing target points, which are closest to a position to be scanned of the object, to emit the ray beam toward the position, for scanning the object to be inspected; and
    a movable stage (1) configured to carry the back scattering scanner, the detector and the controller and being movable with respect to the object to be inspected in a direction perpendicular to a direction in which the detector faces the object to be inspected;
    wherein the back scattering scanner, the detector and the controller perform an imaging security inspection operation on the object to be inspected during moving along with the movable stage with respect to the object.

2. The mobile back scattering imaging security inspection apparatus according to claim 1, wherein the plurality of target points (201) are arranged in one row in a direction perpendicular to a movement direction of the movable stage (1).

3. The mobile back scattering imaging security inspection apparatus according to claim 2, wherein the controller (4) is configured to control the back scattering scanner such that the plurality of target points emit the pencil ray beams sequentially in a predetermined order.

4. The mobile back scattering imaging security inspection apparatus according to claim 3, wherein the controller (4) is configured to control the back scattering scanner (2) such that only one of the plurality of target points emits the pencil ray beam at a time during scanning the object to be inspected.

5. The mobile back scattering imaging security inspection apparatus according to claim 3, wherein the controller (4) is configured to control the back scattering scanner (2) such that at least two of the plurality of target points emit the pencil ray beams at a time during scanning the object to be inspected.

6. The mobile back scattering imaging security inspection apparatus according to claim 5, wherein the mobile back scattering imaging security inspection apparatus is provided with a plurality of the distance measuring devices.

7. The mobile back scattering imaging security inspection apparatus according to claim 6, wherein the controller (4) is configured to determine the target points, from which the pencil ray beams are simultaneously emitted, among the plurality of target points, on the basis of the distance measured by the distance measuring devices.

8. The mobile back scattering imaging security inspection apparatus according to claim 6, wherein the distance measuring devices (101) are configured to measure a height of the object to be inspected such that the controller (4) controls the target point (201) at the corresponding height to emit the ray beam according to the detected height of the object.

9. The mobile back scattering imaging security inspection apparatus according to claim 1, wherein the controller (4) is configured to control the back scattering scanner such that the plurality of target points emit the pencil ray beams sequentially in a predetermined order.

10. The mobile back scattering imaging security inspection apparatus according to claim 9, wherein the controller (4) is configured to control the back scattering scanner (2) such that only one of the plurality of target points emits the pencil ray beam at a time during scanning the object to be inspected.

11. The mobile back scattering imaging security inspection apparatus according to claim 9, wherein the controller (4) is configured to control the back scattering scanner (2) such that at least two of the plurality of target points emit the pencil ray beams at a time during scanning the object to be inspected.

12. The mobile back scattering imaging security inspection apparatus according to claim 11, wherein the mobile back scattering imaging security inspection apparatus is provided with a plurality of the distance measuring devices.

13. The mobile back scattering imaging security inspection apparatus according to claim 12, wherein the controller (4) is configured to determine the target points, from which the pencil ray beams are simultaneously emitted, among the plurality of target points, on the basis of the distance measured by the distance measuring devices.

14. The mobile back scattering imaging security inspection apparatus according to claim 12, wherein the distance measuring devices (101) are configured to measure a height of the object to be inspected such that the controller (4) controls the target point (201) at the corresponding height to emit the ray beam according to the detected height of the object.

15. The mobile back scattering imaging security inspection apparatus according to claim 1, wherein the detector (3) comprises a plurality of strip detecting units (301) arranged in a direction perpendicular to a movement direction of the movable stage (1).

16. The mobile back scattering imaging security inspection apparatus according to claim 15, wherein a collimator (310) is arranged and inserted into a certain depth between every two detecting units, and configured to reduce mutual interference of the back scattering rays at different flying spots on the object to be inspected.

17. A method for performing a mobile back scattering imaging security inspection operation by using a mobile back scattering imaging security inspection apparatus, the apparatus comprising: a back scattering scanner (2) configured to emit a ray beam for scanning an object to be inspected, a detector (3) configured to receive a back scattering ray of the ray beam for scanning the object to be inspected, a controller (4), a movable stage (1) configured to carry the back scattering scanner, the detector and the controller, and a distance measuring device configured to measure in real-time the distance between a surface of the detector for receiving the back scattering ray and a ray incidence face of the object to be inspected, wherein the back scattering scanner (2) comprises a distributed X-ray source and a collimator (210), the distributed X-ray source comprising a plurality of target points (201), rays emitted from each of the target points being collimated by the collimator into at least one pencil ray beam, the method comprising:
  (a) positioning a ray face of the movable stage (1) to face towards a surface to be inspected of an object to be inspected with a certain distance provided therebetween;
  (b) moving the movable stage (1) in a predetermined direction with respect to the object while keeping the ray face of the movable stage (1) parallel to the surface to be inspected, the predetermined direction being perpendicular to a direction in which a surface of the detector for receiving the back scattering ray faces the surface to be inspected of the object;
  (c) measure in real-time, by the distance measuring device, the distance between the surface of the detector for receiving the back scattering ray and the surface to be inspected of the object;
  (c') selecting and controlling, by the controller based on the distance measured by the distance measuring device, one or more of the plurality of outgoing target points, which are closest to a position on the surface to be inspected of the object, to emit the ray beam toward the position, so as to achieve scanning of a row of flying spots corresponding to the plurality of target points (201) on the object to be inspected and to acquire pixel data of the row of flying spots; and
  (d) scanning a region to be inspected of the object to be inspected row by row by using the back scattering scanner (2) as the movable stage (1) moves with respect to the object, and splicing the pixel data of each row of flying points by the controller (4) into an entire image of the region being inspected.

18. The method according to claim 17, wherein in the step (b), the movable stage (1) is kept stationary while the object to be inspected moves in a predetermined direction with respect to the movable stage (1).

19. The method according to claim 17, wherein the distance measuring devices (101) are configured to measure a height of the object to be inspected and the controller (4) is configured to control the target point (201) with a corresponding height to emit the ray beam according to the detected height of the object.

* * * * *